United States Patent
Jan et al.

(10) Patent No.: US 8,350,111 B2
(45) Date of Patent: Jan. 8, 2013

(54) METHOD FOR PRODUCING CUMENE

(75) Inventors: Deng-Yang Jan, Elk Grove Village, IL (US); Christopher Lepine Standing, Chicago, IL (US); James Albert Johnson, Burr Ridge, IL (US); Margo W. Steward, Chicago, IL (US); Mathias P. Koljack, Gilberts, IL (US)

(73) Assignee: UOP LLC, Des Plaines, IL (US)

( * ) Notice: Subject to any disclaimer, the term of this patent is extended or adjusted under 35 U.S.C. 154(b) by 323 days.

(21) Appl. No.: 12/903,177

(22) Filed: Oct. 12, 2010

(65) Prior Publication Data
US 2012/0088937 A1  Apr. 12, 2012

(51) Int. Cl.
C07C 6/12 (2006.01)

(52) U.S. Cl. ...................................................... 585/475
(58) Field of Classification Search ................... 585/475
See application file for complete search history.

(56) References Cited

U.S. PATENT DOCUMENTS

| | | | |
|---|---|---|---|
| 3,308,069 A | 3/1967 | Wadlinger et al. | |
| 5,013,699 A | 5/1991 | Vassilakis et al. | |
| 5,149,894 A | 9/1992 | Holtermann et al. | |
| 5,877,384 A | 3/1999 | Gimpel et al. | |
| 6,756,030 B1 | 6/2004 | Rohde et al. | |
| 7,371,910 B2 | 5/2008 | Yeh et al. | |
| 7,385,098 B2 | 6/2008 | Nanda | |
| 7,517,825 B2 | 4/2009 | Reynolds et al. | |
| 7,700,511 B2 | 4/2010 | Reynolds et al. | |
| 2003/0204121 A1 | 10/2003 | Miller | |
| 2008/0167508 A1 | 7/2008 | Clark et al. | |
| 2008/0171649 A1 | 7/2008 | Jan et al. | |
| 2008/0171900 A1 | 7/2008 | Schmidt | |
| 2008/0171901 A1 | 7/2008 | Reynolds et al. | |
| 2008/0171902 A1 | 7/2008 | Jan et al. | |
| 2008/0194890 A1 | 8/2008 | Brown | |
| 2008/0194898 A1 | 8/2008 | Sohn et al. | |
| 2008/0262279 A1 | 10/2008 | Chen et al. | |
| 2009/0023967 A1 | 1/2009 | Sohn et al. | |
| 2009/0173615 A1 | 7/2009 | Smith | |

OTHER PUBLICATIONS

Brunauer et al., "Adsorption of Gases in Multimolecular Layers", J. Am. Chem. Soc., 1938, vol. 60, No. 2, pp. 309-319.
Kondamudi et al., "Transalkylation of Diisopropylbenzene with Benzene over SAPO-5 Catalyst: A Kinetic Study", Journal of Chemical Technology and Biotechnology, 2008, vol. 83, No. 5, pp. 699-706.
Lei et al., "Process Optimization on Alkylation of Benzene with Propylene", Energy & Fuels, 2009, vol. 23, No. 6, pp. 3159-3166.
Perego et al., "Combining Alkylation and Transalkylation for Alkylaromatic Production", Green Chemistry, 2004, vol. 6, No. 6, pp. 274-279.
Sotelo et al., "A Comp. Study on Transalkylation of Diisopropylbenzene w/Benzene over Several Zeolitic Materials in Supercritical CO2", Applied Catalysis A: General, 2006, vol. 312, pp. 194-201.
Tsai et al., "Disproportionation and Transalkylation of Alkylbenzenes over Zeolite Catalysts", Applied Catalysis A: General, 1999, vol. 181, No. 2, pp. 355-398.

*Primary Examiner* — Thuan D Dang
(74) *Attorney, Agent, or Firm* — Mark R Willis

(57) ABSTRACT

One exemplary embodiment can be a method for processing polyisopropylbenzene for producing cumene. The method can include passing a transalkylation feed stream to a transalkylation zone, and passing a reaction product to a separation zone. Typically, the separation zone produces a stream including di-isopropylbenzene, tri-isopropylbenzene, and one or more heavy compounds. Moreover, the stream may include at least about 0.7%, by weight, of the one or more heavy compounds based on the weight of the di-isopropylbenzene, tri-isopropylbenzene, and the one or more heavy compounds in the stream, and at least a portion of the stream is recycled to the transalkylation zone.

16 Claims, 5 Drawing Sheets

METHOD FOR PRODUCING CUMENE

FIELD OF THE INVENTION

This invention generally relates to a method for producing cumene.

DESCRIPTION OF THE RELATED ART

Cumene synthesis can often include sections for transalkylation and separation of reaction products. Often, di-isopropylbenzene (hereinafter may be abbreviated "DIPB") and tri-isopropylbenzene (hereinafter may be abbreviated "TIPB") produced in a transalkylation reactor may be recovered and recycled to produce additional cumene. Often, heavier substituted aromatics having boiling points similar to or greater than DIPB and TIPB are separated with these compounds. As such, these heavier substituted aromatics may be purged along with some DIPB and TIPB because these heavier substituted aromatics can be precursors for the unwanted production of ethylbenzene (hereinafter may be abbreviated "EB"). Particularly, EB can be separated along with the cumene, and thus, require additional subsequent separation processes for purifying the cumene product. As an example, if the cumene is converted into phenol, then the EB can interfere with that reaction. So, a subsequent process is typically utilized to remove the EB, thus increasing manufacturing costs and reducing the efficiency of the process.

Often, the recoveries of DIPB and TIPB are limited to achieve a high purity of cumene. As such, a heavy stream is typically purged from the separation section to minimize the inclusion of heavier substituted aromatics besides DIPB and TIPB that can be precursors to EB in the transalkylation section. Generally, separating EB from cumene may be elaborate with appreciable capital and energy cost. Furthermore, purging this heavy stream from the unit can result in the loss of DIPB and TIPB that can be recovered and converted into additional cumene. Thus, there is generally a desire to improve the efficiencies of such units to recover the DIPB and particularly TIPB, and convert these compounds into a product, such as cumene, without incurring the undesired production of EB and the associated energy and capital cost for the separation of EB from cumene.

SUMMARY OF THE INVENTION

One exemplary embodiment can be a method for processing polyisopropylbenzene for producing cumene. The method can include passing a transalkylation feed stream to a transalkylation zone, and passing a reaction product to a separation zone. Typically, the separation zone produces a stream including di-isopropylbenzene, tri-isopropylbenzene, and one or more heavy compounds. Moreover, the stream may include at least about 0.7%, by weight, of the one or more heavy compounds based on the weight of the di-isopropylbenzene, tri-isopropylbenzene, and the one or more heavy compounds in the stream, and at least a portion of the stream is recycled to the transalkylation zone.

Another exemplary embodiment may be a method for processing polyisopropylbenzene for producing cumene. The method can include passing a transalkylation feed stream to a transalkylation zone, and passing a reaction product to a separation zone. Typically, the separation zone produces a side-stream including di-isopropylbenzene and a bottom stream including tri-isopropylbenzene and one or more heavy compounds. Generally, at least a portion of the bottom stream is combined with the side-stream and recycled to the transalkylation zone.

Yet another exemplary embodiment can be a method for producing cumene. The method can include passing a transalkylation feed stream to produce a reaction product and passing the reaction product to a separation zone. Usually, the transalkylation feed stream includes benzene, di-isopropylbenzene, tri-isopropylbenzene, and at least about 0.3%, by weight, one or more heavy compounds based on the weight of the feed stream to a transalkylation zone. Generally, the transalkylation zone includes a catalyst having a UZM-8 zeolite and a beta zeolite. Moreover, the separation zone can include a first distillation zone producing an overhead stream including benzene, a second distillation zone producing an overhead stream including cumene, and a third distillation zone producing a bottom stream including di-isopropylbenzene, tri-isopropylbenzene, and the one or more heavy compounds. Typically, at least a portion of the bottom stream is recycled to the transalkylation zone.

The embodiments disclosed herein can provide a scheme for recovering at least a portion of a bottom stream from a separation zone. Particularly, the transalkylation zone receiving the recycle can process not only the DIPB but the TIPB while minimizing the production of impurities, such as EB. Thus, the embodiments disclosed herein can recover DIPB and TIPB without deliberate separation of TIPB from heavier components. Consequently, a significant savings in capital and utility cost can be realized.

In particular, the transalkylation zone can be operated with any suitable catalyst that reduces EB production. In one preferred embodiment, combining a UZM-8 zeolite with a beta zeolite can provide significantly lower EB formation at constant DIPB conversions and better cumene product selectivity. As a consequence, the embodiments disclosed herein can provide a more efficient process by allowing the recovery of DIPB and TIPB from one or more heavier streams from the separation zone and the production of more and higher quality cumene, while minimizing a purge stream of heavier compounds.

DEFINITIONS

As used herein, the term "stream" can include various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. The stream can also include aromatic and non-aromatic hydrocarbons. Moreover, the hydrocarbon molecules may be abbreviated C1, C2, C3 . . . Cn where "n" represents the number of carbon atoms in the one or more hydrocarbon molecules. Furthermore, a superscript "+" or "−" may be used with an abbreviated one or more hydrocarbons notation, e.g., $C3^+$ or $C3^-$, which is inclusive of the abbreviated one or more hydrocarbons. As an example, the abbreviation "$C3^+$" means one or more hydrocarbon molecules of three carbon atoms and/or more.

As used herein, the term "zone" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

As used herein, the term "rich" can mean an amount of at least generally about 30%, preferably about 50%, and more preferably about 70%, by mole, of a compound or class of compounds in a stream.

As used herein, the term "substantially" can mean an amount of at least generally about 80%, preferably about 90%, and optimally about 99%, by mole, of a compound or class of compounds in a stream.

As used herein, the term "cumene" may be used interchangeably with 1-methylethylbenzene or isopropylbenzene.

As used herein, the term normal "propylbenzene" may be abbreviated "nPB".

As used herein, the term "ethylbenzene" may be abbreviated "EB".

As used herein, the term "di-isopropylbenzene" may be abbreviated "DIPB".

As used herein, the term "tri-isopropylbenzene" may be abbreviated "TIPB".

As used herein, the term "polypropylbenzene" may include DIPB and TIPB and be abbreviated 'PIPB".

As used herein, the term "weight ppm" may be abbreviated "wppm".

As used herein, the term "weight hourly space velocity" may be abbreviated "WHSV".

As used herein, the term "diethyldiphenylethane" may be abbreviated "DEDPE".

As used herein, the term "isoprodimettetra" may represent a substituted tetralin having one or more substituent groups of methyl, ethyl, propyl and butyl with the total carbon number of substituent groups of five.

As used herein, the term "hexmetdihyindene" may represent a substituted indene or dihydroindene having one or more substituent groups of methyl, ethyl, propyl, butyl and pentyl with the total carbon number of substituent groups of six.

As used herein, the terms "amylbenzene", "hexylbenzene", and "heptylbenzene" may represent a substituted benzene having one or more substituent groups of methyl, ethyl, propyl, butyl, pentyl, hexyl and heptyl with the total carbon number of substituent groups of, respectively, five, six, and seven.

As used herein, the term "co-boil" may represent one or more compounds having boiling temperatures similar to DIPB and/or TIPB. As such, a co-boiling compound may separate with DIPB and/or TIPB in a process such as distillation, particularly in a side-stream or a bottom stream. Co-boils of DIPB may include N-propylbenzene, butylbenzene, cumene and amylbenzene, and co-boils of TIPB may include α-methylstyrene, hexylbenzenes, heptylbenzenes, hexmetdihyindenes, isoprodimettetras, 2,2-diphenylpropane, and DEDPE.

As used herein, the term "heavy" may be used to refer to aromatics or compounds having boiling points at or greater than DIPB and/or TIPB.

As used herein, the term "heavy compound" may include heavy aromatics, such as one or more n-propylbenzenes, amylbenzenes, cymenes, butylbenzenes, α-methylstyrenes, hexylbenzenes, heptylbenzenes, indenes, tetralins, hexmetdihyindenes, isoprodimettetras, diphenylpropanes, and diphenylethanes, which may be optionally or further substituted; and/or other previously unmentioned co-boils that may separate with DIPB and/or TIPB, such as in a side-stream and/or bottom stream, in processes such as distillation.

As used herein, the terms streams, feeds, products, bottoms, overheads, recycles, lines, and pipes may be used interchangeably when referring to the flow lines in the drawings.

DETAILED DESCRIPTION

Figure 1:
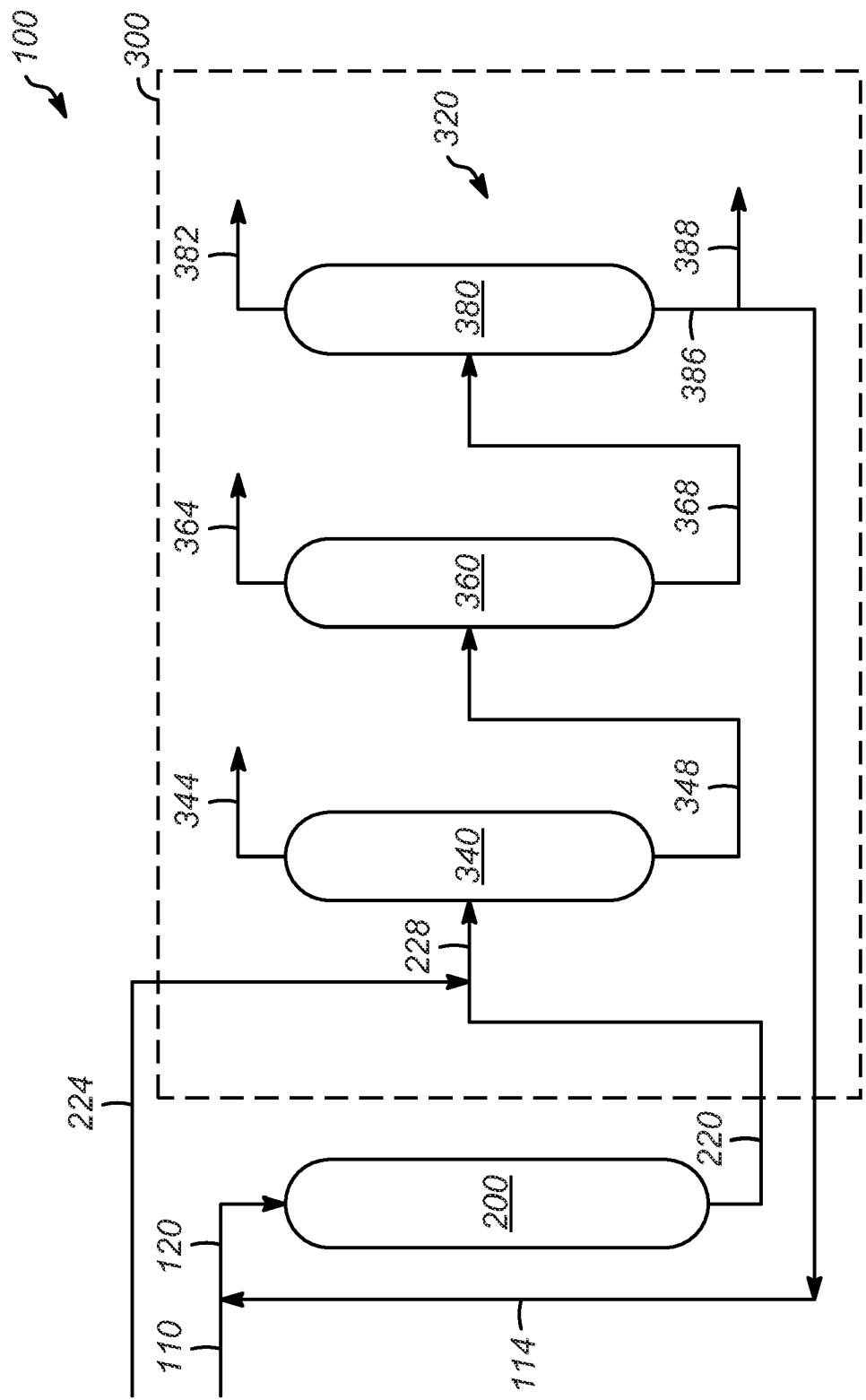
FIG. 1 is a schematic depiction of an exemplary apparatus.

Referring to FIG. 1, an exemplary apparatus 100 can include a transalkylation zone 200 and a separation zone 300. Typically, the separation zone 300 can include any number of distillation zones, such as a plurality of distillation zones 320. In this exemplary embodiment, the plurality of distillation zones 320 can include a first distillation zone 340, a second distillation zone 360, and a third distillation zone 380. Although the separation zone 300 depicts distillation zones, it should be understood that any suitable separation zone or device can be utilized. In this embodiment, the distillation zones 340, 360 and 380 can include a single distillation column, but any suitable number of distillation columns may be utilized. Generally, each distillation zone 340, 360 and 380 can produce respective overhead streams 344, 364, and 382. Particularly, the overhead stream 344 can include an effective amount of or rich in benzene, the overhead stream 364 can include an effective amount of or rich in cumene, and the stream 382 can include an effective amount of or rich in DIPB. These streams 344, 364, and 382 can be described in further detail below.

Generally, a stream 110, including benzene and DIPB, combined with a recycle stream 114, as hereinafter described, can be provided to the transalkylation zone 200. The combined streams 110 and 114 may form a transalkylation feed stream 120. Typically, the feed stream 120 includes an effective amount of benzene and DIPB for producing cumene. Usually, the weight ratio of benzene to DIPB is about 1:5-about 5:1, preferably about 1:3-about 3:1, and optimally about 1.5:1. In addition, other aromatic compounds may be present, such toluene, xylene, nPB, butylbenzene, hexylbenzene, heptylbenzenes, TIPB, and other substituted aromatic rings. Usually, the feed stream 120 contains at least generally about 0.1%, preferably about 1%, and optimally about 2%, by weight, of TIPB based on the weight of the feed stream 120. Moreover, the feed stream 120 can contain at least generally about 0.3%, alternatively about 0.4%, or even about 0.5%, by weight, of one or more heavy compounds, such as n-propylbenzenes, amylbenzenes, cymenes, butylbenzenes, α-methylstyrenes, hexylbenzenes, heptylbenzenes, indenes, tetralins, hexmetdihyindenes, isoprodimettetras, diphenylpropanes, and diphenylethanes, which may be optionally or further substituted; based on the weight of the feed stream 120.

The transalkylation zone 200 can include one or more transalkylation reactors, including any suitable catalyst, to produce cumene. Cumene can be produced under suitable reaction conditions, such as a temperature of about 60-about 390° C., preferably about 100-about 200° C., a pressure of about 100-about 14,000 kPa, preferably about 2,000-about 4,000 kPa, and a WHSV of about 0.1-about 50 $hr^{-1}$, preferably about 0.5-about 5 $hr^{-1}$.

In addition, the transalkylation zone 200 may include any suitable catalyst, or combination of catalysts. The catalyst can be in a single catalyst pellet or separate catalyst pellets with the latter being a physical mixture or a stacked configuration. Particularly, the catalyst can include a first component and a second component.

One such catalyst can be a UZM-8 zeolite. Generally, the UZM-8 is a microporous crystalline zeolite, typically aluminosilicate. One exemplary UZM-8 zeolite can have an empirical formula:

$$R_r^{p+}Al_{1-x}E_xSi_yO_z$$

where "R" is at least one organoammonium cation selected from the group consisting of protonated amines, protonated diamines, quaternary ammonium ions, diquaternary ammonium ions, protonated alkanolamines and quaternized alkanolammonium ions. Preferred organoammonium cations are those that are non-cyclic or those that do not contain a cyclic group as one substituent. Of these, those that contain at least two methyl groups as substituents are especially preferred. The ratio of "R" to (Al+E) is represented by "r" which varies from about 0.05-about 5. The value of "p" which is the weighted average valence of "R" varies from about 1-about 2. The ratio of Si to (Al+E) is represented by "y" that varies from about 6.5-about 35. Element "E" is tetrahedrally coordinated, present in the framework, and selected from the group consisting of gallium, iron, chromium, indium and boron. The mole fraction of "E" is represented by "x" and has a value of about 0-about 0.5, while "z" is the mole ratio of 0 to (Al+E) and is given by the equation:

$$z=(r \cdot p+3+4 \cdot y)/2$$

This and other UZM-8 zeolites, as well as methods of making, are disclosed in, e.g., U.S. Pat. No. 6,756,030 B1.

Another catalyst can be a beta zeolite. Such a beta zeolite is disclosed in, e.g., U.S. Pat. No. 7,371,910 B2 and U.S. Pat. No. 3,308,069. The composition of the beta zeolite may be expressed as mole ratios of oxides as:

$$0.1 \text{ to } 0.3R:0.7 \text{ to } 1.0M_{2/n}O:1\ Al_2O_3:2.5 \text{ to } 4.0SiO_2.YH_2O$$

where "R" is selected from the group consisting of a ethyl ammonium oxide, hydrogen oxide and mixtures thereof with one another; "M" is a metal and "n" is the valence thereof and "Y" is a value from about 3.5-about 5.5.

Suitable combinations of catalytic materials may be used. In one exemplary embodiment, a combination of UZM-8 zeolite and beta zeolite can be utilized in any effective weight ratio. In one exemplary embodiment, the weight ratio of UZM-8 zeolite to beta zeolite may range from about 1:10-about 10:1, preferably about 1:5-about 5:1. Utilizing catalysts that effectively react DIPB and TIPB can allow the recovery of additional amounts of DIPB and TIPB while minimizing the production of unwanted EB. Although not wanting to be bound by theory, it is believed that the combination of UZM-8 zeolite and beta zeolite is an improvement as they are less likely to convert heavy compounds like indene and tetralin into EB.

In addition, the catalyst can be an acid-treated steam-modified Y zeolite, a chemically-modified Y zeolite, or a combination thereof. The acid-treated steam-modified Y zeolite may be a crystalline zeolitic molecular sieve, and can have a unit cell size of about 24.34-about 24.58 Å and a bulk $Si/Al_2$ molar ratio of about 6.5-about 20. The chemically-modified Y zeolite may be expressed as mole ratios of oxides by the following formula:

$$(0.85-1.1)M_{2/n}O:Al_2O_3:xSiO_2$$

wherein "M" is a cation having the valence "n" and "x" and has a value of about 5.0-about 11.0. Such zeolites are disclosed in, e.g., US 2008/0171649 A1, US 2008/0171901 A1, and US 2008/0171902 A1.

Afterwards, a reaction product stream 220 can exit the transalkylation zone 200 and enter the separation zone 300. The separation zone 300 can receive an alkylation effluent 224, including one or more C6-C15 hydrocarbons, to form a combined stream 228 that enters the first distillation zone 340. Generally, the first distillation zone 340 can produce the overhead stream 344 and a bottom stream 348. The bottom stream 348 can be routed to the second distillation zone 360 which, in turn, produces the overhead stream 364 and a bottom stream 368. Afterwards, the bottom stream 368 can enter the third distillation zone 380, and produce the overhead stream 382 and a bottom stream 386. At least a portion of the bottom stream 386, including DIPB and TIPB, can form the recycle stream 114 and be combined to form the feed stream 120 that includes an effective amount of benzene for conducting the transalkylation reaction. In addition, the bottom stream 386 can include one or more heavy compounds, such as one or more n-propylbenzenes, amylbenzenes, cymenes, butylbenzenes, α-methylstyrenes, hexylbenzenes, heptylbenzenes, indenes, tetralins, hexmetdihyindenes, isoprodimettetras, diphenylpropanes, and diphenylethanes, which may be optionally or further substituted, and compounds with a boiling point about at or above di-isopropylbenzene and/or tri-isopropylbenzene based on the weight of the stream 386. Generally, these one or more heavy compounds can comprise at least about 0.7%, about 0.8%, or even about 1.0%, by weight, based on the sum of DIPB, TIPB and heavy compounds recovered from the third distillation zone 380, such as in the bottom stream 386. Further still, these one or more heavy compounds can comprise about 0.7-about 2%, by weight, based on the sum of DIPB, TIPB and heavy compounds recovered from the third distillation zone 380, such as in the bottom stream 386. A purge stream 388 can be taken to prevent the undesired accumulation of heavy compounds that may separate with DIPB and/or TIPB. As noted above, EB can exit with cumene and require separation before undertaking downstream processing to convert cumene into desirable products, such as phenol. Thus, the embodiments disclosed herein can minimize the unwanted production of EB.

Figure 2:
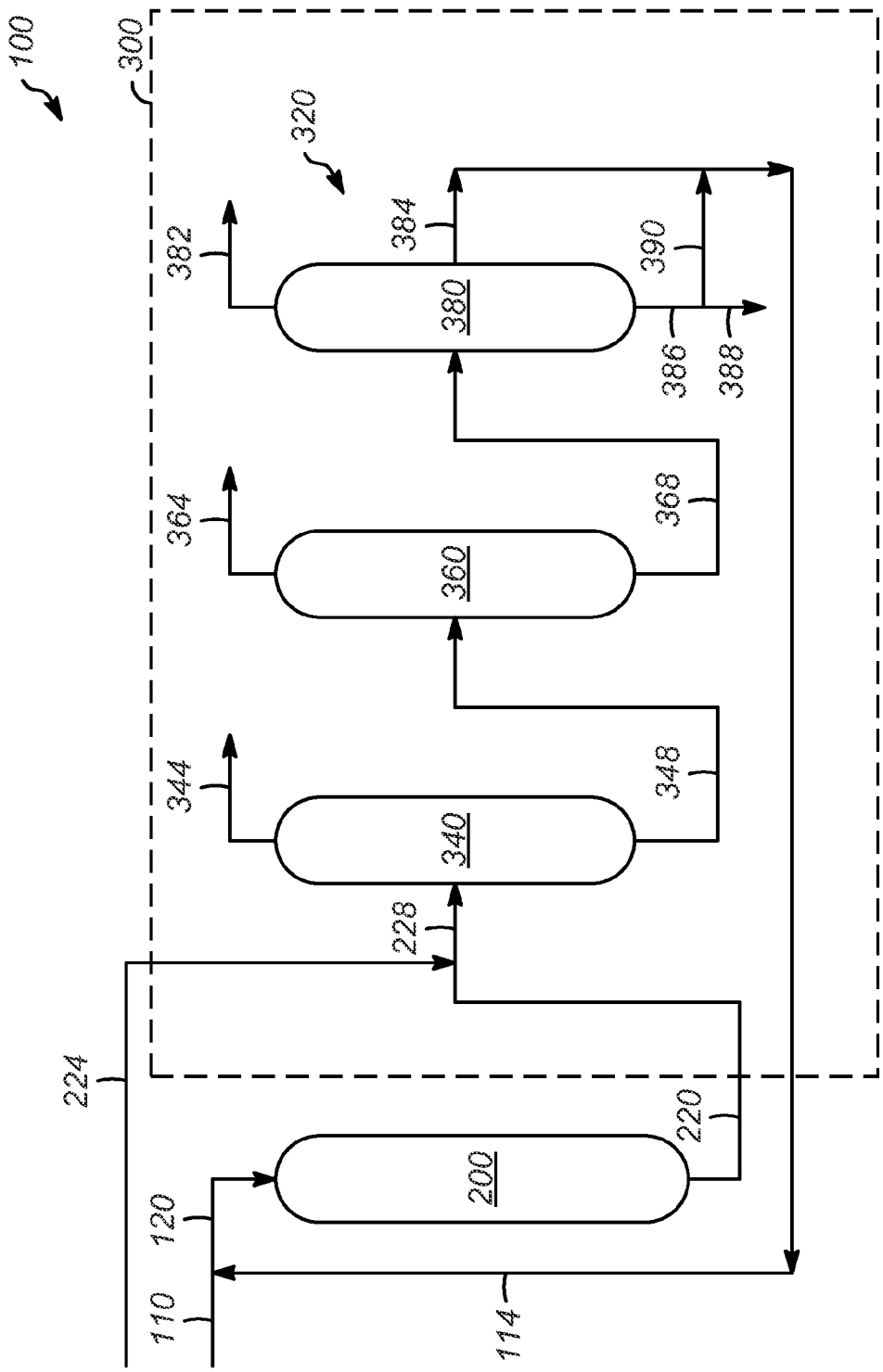
FIG. 2 is a schematic depiction of another version of the exemplary apparatus.

Referring to FIG. 2, another version of the exemplary apparatus 100 is depicted. In this exemplary apparatus, the third distillation zone 380 can provide the overhead stream 382, which can contain at least about 1% of co-boils of DIPB, such as N-propylbenzene, amylbenzene, cymene, and/or butylbenzene, the bottom stream 386, as well as a side-stream 384. Generally, a portion of the bottom stream 386, namely a split stream 390, can be combined with the side-stream 384 to form the recycle stream 114. The purge stream 388 can also be taken from the bottom stream 386. In this exemplary embodiment, the third distillation zone 380 can produce the side-stream 384 which can separate the DIPB from the TIPB. Thus, the third distillation zone 380 allows the further separation of desirable products, namely the DIPB from the TIPB, and compounds with a boiling point about at or above tri-isopropylbenzene based on the weight of the stream, and thus, further allows efficiency improvements in the exemplary apparatus 100.

ILLUSTRATIVE EMBODIMENTS

The following examples are intended to further illustrate the subject catalyst. These illustrations of embodiments of the invention are not meant to limit the claims of this invention to the particular details of these examples. These examples are based on engineering calculations and actual operating experience with similar processes.

Comparison Catalyst A

A commercially available steamed Y zeolite, as disclosed in U.S. Pat. No. 5,013,699, is slurried in a 15%, by weight, NH$_4$NO$_3$ aqueous solution. A sufficient quantity of a 17 wt % HNO$_3$ solution is added over a period of 30 minutes to remove part of the extra-framework aluminum. Thereafter, the slurry temperature is heated up to 79° C. and maintained for 90 minutes. After 90 minutes of contact at 79° C., the slurry is filtered and the filter cake is washed with a 22%, by weight, ammonium nitrate solution followed by a water wash with an excessive amount of warm de-ionized water. The resulting filter cake is dried to an appropriate moisture level, mixed with HNO$_3$-peptized alumina, sold under the trade designation CATAPAL C and is obtained from Sasol North America, a subsidiary of Sasol Limited of Gauteng, South Africa, to give a mixture of 80 parts, by weight, of zeolite and 20 parts, by weight, Al$_2$O$_3$ binder on a dry basis. Afterwards, the mixture is extruded into 1.59 mm diameter cylindrical extrudates, dried, and calcined at approximately 600° C. for one hour in flowing air. Properties of the catalyst are 65.2 wt % SiO$_2$ on a bulk and dry basis, 34.7 wt % Al$_2$O$_3$ on a dry basis, 0.04 wt % sodium calculated as Na$_2$O on a dry basis, 0.1 wt % (NH$_4$)$_2$O on a dry basis, a unit cell size of 24.512 Å, and an absolute XRD intensity of 69.7 conducted according to the x-ray analysis at columns 7-8 of U.S. Pat. No. 6,756,030 B1.

Catalyst B

In a large beaker, 160.2 grams of diethyldimethylammonium hydroxide are added to 1,006.69 grams of de-ionized water, followed by 2.1 grams of 50%, by weight, NaOH solution. Next, 51.5 grams of liquid sodium aluminate are added slowly and stirred for 20 minutes. Subsequently, 178.9 grams of silica, sold under the trade designation ULTRA-SIL® by Evonik Degussa GmbH of Frankfurt, Germany, are slowly added to the gel and stirred for 20 minutes. Next, 36 grams of UZM-8 seed, such as made according to U.S. Pat. No. 6,756,030 B1, are added to the gel and stirred for an additional 20 minutes. The gel is then transferred to a 2-liter stirred reactor and heated to 160° C. for 2 hours, and crystallized for 115 hours.

After digestion, the material is filtered and washed with de-ionized water and dried at 100° C. An X-Ray Diffraction (hereinafter abbreviated "XRD") analysis, conducted according to the x-ray analysis at columns 7-8 of U.S. Pat. No. 6,756,030 B1, shows a substantially pure UZM-8 material. The elemental analysis by inductively coupled plasma-atomic emission spectroscopy (herein may be abbreviated "ICP-AES") according to UOP method 961-98, is Si=42.2%, Al=4.0%, and Na=1.8%, corresponding to Si/Al$_2$=20.3, and C=6.5%, H=3.1%, and N=1.2% with all values by weight.

UZM-8 zeolite is dried at 100° C. for 12 hours and extruded into pellets of cylindrical extrudate of 0.159 cm diameter containing 70% zeolite and 30% alumina on a volatile free basis. The formed catalyst is dried at 110° C. for 2 hours, and calcined in a rotary kiln at about 600° C. for about 1 hour in flowing air. The calcined extrudate is ammonium exchanged using an ammonium nitrate solution of about 10%, by weight, at about 65° C. for 2 hours to lower the sodium content below 1,000 wppm as Na$_2$O on a volatile free basis. Afterwards, the calcined extrudate is dried at about 100° C. for 2 hours to produce a dried, ion exchanged extrudate. The surface area and pore volume are calculated using nitrogen partial pressure p/p$_O$ data points ranging from about 0.03-about 0.30 using the BET (Brunauer-Emmett-Teller) model method using the nitrogen adsorption technique as described in ASTM D4365-95, Standard Test Method for Determining Micropore Volume and Zeolite Area of a Catalyst, and in the article by S. Brunauer et al., J. Am. Chem. Soc., 60(2), 309-319 (1938).

Catalyst C

A synthesized beta zeolite, such as a beta zeolite disclosed in U.S. Pat. No. 7,371,910 B2, is first ammonium exchanged to lower its sodium content below 500 wppm as Na$_2$O on a volatile free basis and dried at 100° C. The ammonium exchanged and dried beta zeolite is extruded into cylindrical pellets of 0.159 cm diameter containing 70%, by mass, zeolite and 30%, by mass, alumina on a volatile free basis. The formed catalyst is dried at 110° C. for 2 hours, and calcined in a rotary kiln at about 600° C. for about 1 hour in flowing air.

Catalyst D

Synthesized UZM-8 prepared as described above for Catalyst B is ammonium exchanged to lower sodium content to less than 500 wppm as Na$_2$O on a volatile free basis. The ammonium exchanged UZM-8 is mixed with ammonium-exchanged beta zeolite as described in Catalyst C preparation and has a 70:30 weight ratio, which is then extruded in 0.159 cm diameter cylinder. The extrudate is dried at 100° C. for 2 hours. Next, the extrudate is calcined at 450° C. for 1 hour and then 550° C. for another hour in a flowing air.

Catalysts are tested for transalkylation performance using a feed containing benzene and polyalkylated benzenes in the following manner:

TABLE 1

| Catalyst | A | D | E | F |
|---|---|---|---|---|
| Catalyst | A | A single particle of Catalyst D | A physical mixture of Catalyst B and C at a weight ratio of 30/70 | Stacked Catalyst B (lead) and Catalyst C (lag) at a weight ratio of 40/60 |

As depicted in the table, Catalysts B and C are combined in different weight ratios and the combinations re-labeled, respectively, as Catalysts E and F.

The feed is prepared by blending polyalkylated benzenes obtained from one or more commercial transalkylation units with benzene. The feed blend represents a typical transalkylation feed composition with an aromatic ring group to propyl group molar ratio of approximately 2.0:1.0.

Three feed blends are used in assessing the efficiency of process flows in recovering DIPB and TIPB. The first feed blend contains benzene and DIPB and represents a case where only DIPB is recovered, while TIPB and heavy compounds are rejected. The second feed blend is prepared by incorporating a stream containing TIPB from the bottom of a commercial PIPB column, which contains heavy compounds including one or more hexylbenzenes, heptylbenzenes, substituted or unsubstituted indenes, tetralins, diphenylethanes, diphenylpropanes and other similar boiling compounds, into the first feed blend. This feed is used to model the recovery of TIPB without elaborate separation of TIPB from the heavy compounds. The third feed blend is prepared by incorporating 1,3,5-tri-isopropylbenzene purchased from Sigma-Aldrich of St. Louis, Mo. into the first feed blend, which models an "ideal" recovery of TIPB, while excluding many of the heavy compounds. The feed composition as measured by gas chromatography is summarized in Table 2 below.

TABLE 2

| Feed Blend | Bz/DIPB %, by weight | Bz/DIPB/PIPB Bottom %, by weight | Bz/DIPB/TIPB %, by weight |
|---|---|---|---|
| Non-aromatics | 0.038 | 0.029 | 0.032 |
| Benzene | 59.051 | 59.261 | 57.261 |
| Toluene | 0.000 | 0.003 | 0.003 |
| Ethylbenzene | 0.000 | 0.000 | 0.000 |
| Xylene | 0.002 | 0.001 | 0.002 |
| Cumene | 1.382 | 1.025 | 1.085 |
| N-Propylbenzene | 0.003 | 0.003 | 0.003 |
| Butylbenzene | 0.006 | 0.005 | 0.005 |
| Cymene | 0.002 | 0.009 | 0.009 |
| Amylbenzene | 0.004 | 0.003 | 0.003 |
| Di-isopropylbenzene | 39.252 | 37.067 | 39.468 |
| α-Methylstyrene | 0.001 | 0.001 | 0.001 |
| Hexylbenzenes | 0.165 | 0.162 | 0.000 |
| Heptylbenzenes | 0.032 | 0.023 | 0.025 |
| Tri-isopropylbenzene | 0.017 | 2.061 | 2.008 |
| Hexmetdihyindenes | 0.001 | 0.066 | 0.016 |
| Isoprodimettetras | 0.000 | 0.014 | 0.001 |
| Others | 0.043 | 0.174 | 0.076 |
| 22-Diphenylpropane | 0.000 | 0.048 | 0.001 |
| DEDPE | 0.000 | 0.045 | 0.000 |
| Unknowns | 0.000 | 0.000 | 0.000 |
| Sum of Heavy Compounds | 0.254 | 0.550 | 0.137 |
| Sum of DIPB, TIPB, and Heavy Compounds | 39.523 | 39.678 | 41.613 |

The heavy compounds in Table 2 is the summation of the weight percents of N-propylbenzene, butylbenzene, cymene, amylbenzene, α-methylstyrene, hexylbenzenes, heptylbenzenes, hexmetdihyindenes, isoprodimettetras, others, 22-diphenylpropane, DEDPE, and unknowns. The TIPB and heavy compounds weight ratio, as depicted in Table 3 below, is determined by dividing, respectively, TIPB and heavy compounds, by the combined weight of DIPB, TIPB, and heavy compounds:

TABLE 3

| Feed Blend | Bz/DIPB Weight/ Weight | Bz/DIPB/PIPB Bottom Weight/ Weight | Bz/DIPB/TIPB Weight/ Weight |
|---|---|---|---|
| TIPB/(DIPB + TIPB + Heavy Compounds) | 0.00043 | 0.052 | 0.048 |
| Heavy Compounds/(DIPB + TIPB + Heavy Compounds) | 0.0064 | 0.014 | 0.0033 |

As depicted in Table 3, the Bz/DIPB/PIPB Bottom feed for transalkylation can include at least about 5%, by weight, TIPB, and at least about 1%, by weight, heavy compounds, based on the sum of DIPB, TIPB, and heavy compounds.

Comparison Examples 1-3 and Examples 1-6

The catalysts and feeds are tested as depicted in Table 4 as depicted below:

TABLE 4

| | Catalyst | Feed |
|---|---|---|
| Comparison Example 1 | A | Bz/DIPB |
| Comparison Example 2 | A | Bz/DIPB/PIPB bottom |
| Comparison Example 3 | A | Bz/DIPB |
| Example 1 | D | Bz/DIPB |
| Example 2 | D | Bz/DIPB/PIPB bottom |
| Example 3 | D | Bz/DIPB/TIPB |

TABLE 4-continued

| | Catalyst | Feed |
|---|---|---|
| Example 4 | F | Bz/DIPB |
| Example 5 | E | Bz/DIPB |
| Example 6 | E | Bz/DIPB/PIPB bottom |

The tests are done in a fixed bed reactor in a once-through mode under conditions of 3,548 kPa reactor pressure, a molar ratio of aromatic ring groups to propyl group of 2.0:1.0, and a 0.8 hr$^{-1}$ DIPB WHSV over a range of reaction temperatures from about 100-about 150° C. The reactor is allowed to achieve essentially steady-state conditions at each reaction temperature, and the product is sampled for analysis. Essentially no catalyst deactivation occurs during the test. Prior to introducing the feed, each catalyst is subjected to a drying procedure by contact with a flowing nitrogen stream containing less than 10 wppm water at 250° C. for 6 hours, or a flowing benzene stream at 260° C. for 24-48 hours. Four separate runs are made with results from the first run for Comparison Examples 1-2 and from the second run for Examples 1-3 depicted in FIGS. 3-4, and results from the third run for Comparison Example 3 and from the fourth run for Examples 4-6 depicted in FIG. 5.

Figure 3:
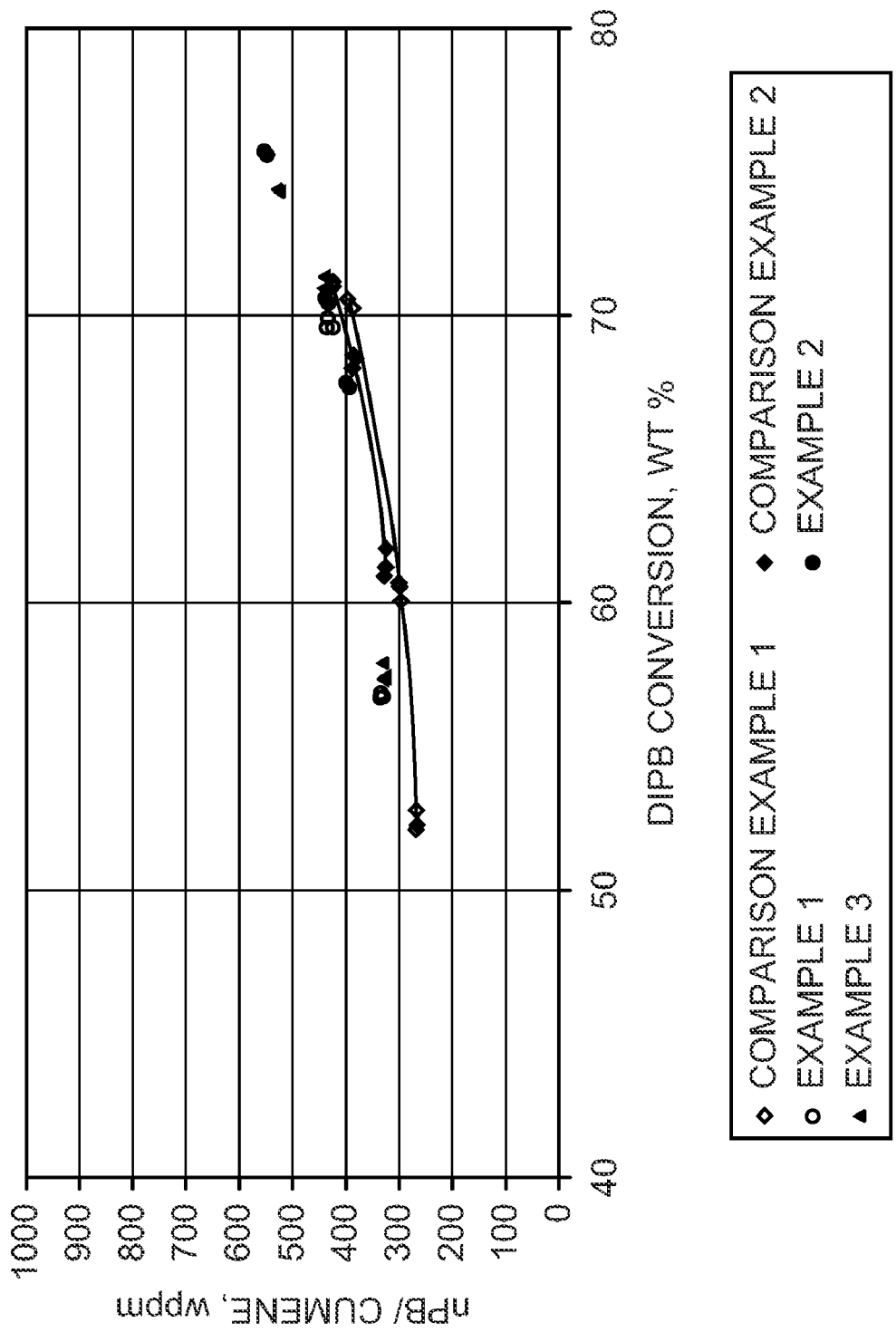
FIG. 3 is a graphical depiction of experimental results depicting nPB/cumene ratio versus DIPB conversion.
Figure 4:
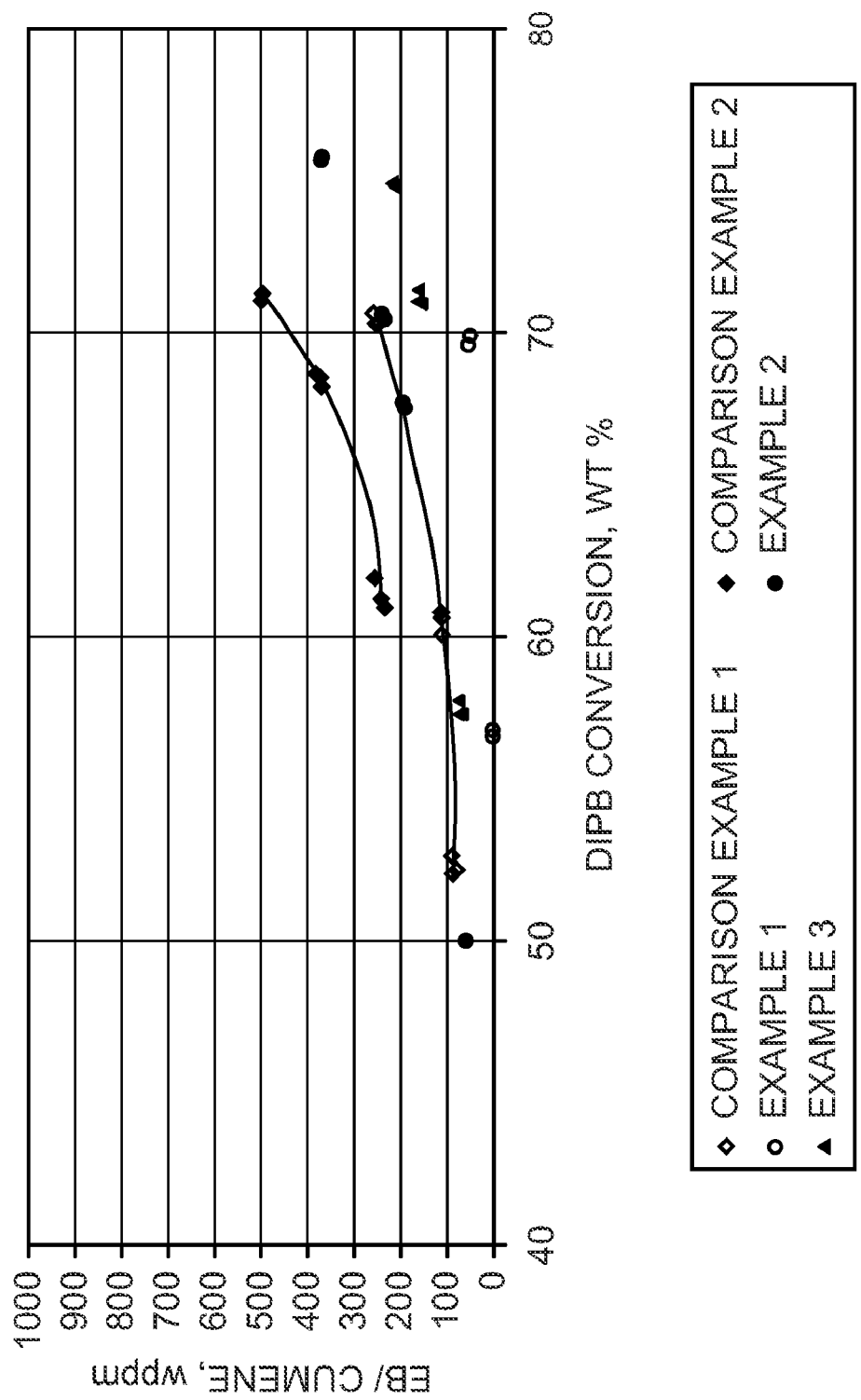
FIG. 4 is a graphical depiction of experimental results depicting EB/cumene ratio versus DIPB conversion.
Figure 5:
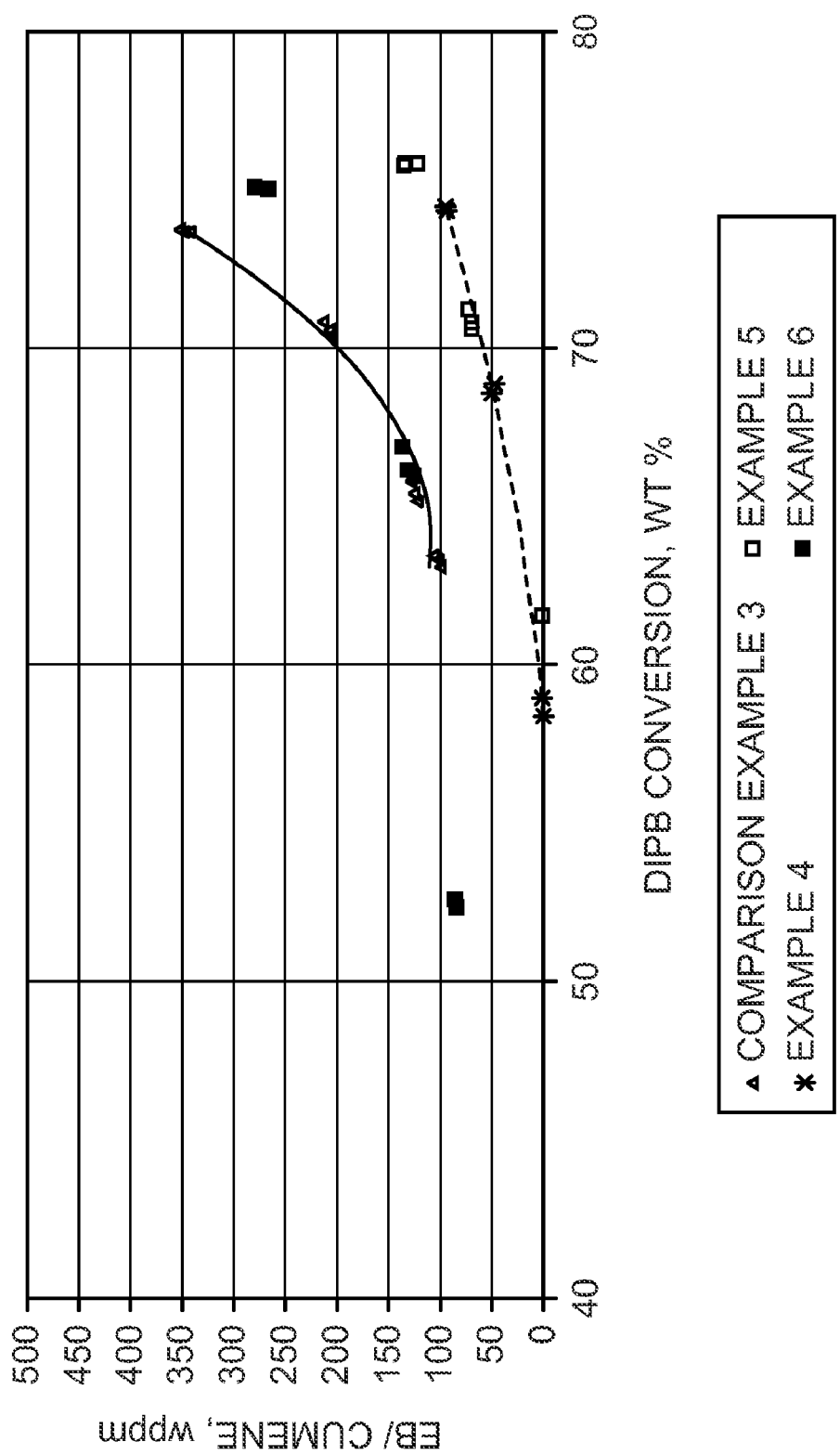
FIG. 5 is another graphical depiction of experimental results depicting EB/cumene ratio versus DIPB conversion.

Referring to FIG. 3, the contents of nPB are relatively stable over a wide range of DIPB conversions. Referring to FIGS. 4-5, the contents of EB formed in the product are also relatively stable over a range of DIPB conversions. When simulating the recovery of TIPB using the second feed blend containing the commercial PIPB column bottom, the contents of nPB and EB are comparable or increase slightly in comparison with a feed blend that contains mostly pure TIPB over a range of DIPB conversions. Although not wanting to be bound by theory, this is unexpected because one would expect the heavy compounds in the PIPB column bottom containing 2-ring aromatics, such as substituted indene and tetralins, to significantly reduce the catalyst activity and increase nPB and EB contents at a given DIPB conversion. The data supports the PIPB recovery as depicted in FIGS. 3 and 4, where a deliberate distillation/separation of TIPB from heavy compounds is not required. The data provides that the process can operate with a poly-alkylate feed composition that contains primarily DIPB, TIPB and at least about 0.3%, by weight, of heavy compounds going into the transalkylation reactor. Thus, utilizing catalysts disclosed herein can provide the same advantages when processing feeds with substantially lower or higher molar feed ratios.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing, all temperatures are set forth in degrees Celsius and, all parts and percentages are by weight, unless otherwise indicated.

From the foregoing description, one skilled in the art can easily ascertain the essential characteristics of this invention and, without departing from the spirit and scope thereof, can make various changes and modifications of the invention to adapt it to various usages and conditions.

The invention claimed is:
1. A method for processing polyisopropylbenzene for producing cumene, comprising:
A) passing a transalkylation feed stream containing benzene and a recycle stream to a transalkylation zone com- prising a catalyst having a first component comprising UZM-8 zeolite and a second component comprising beta zeolite, wherein a weight ratio of the first component to the second component is about 30:70 to about 70:30 under transalkylation conditions to produce a product comprising cumene; and B) passing the reaction product to a separation zone for separating cumene, wherein the separation zone produces a stream comprising di-isopropylbenzene, tri-isopropylbenzene, and one or more heavy compounds comprising at least one of a hexylbenzene, a heptylbenzene, an indene, a tetralin, a diphenylethane, and a diphenylpropane, wherein the stream comprises at least about 0.7%, by weight, of the one or more heavy compounds based on the weight of the di-isopropylbenzene, tri-isopropylbenzene, and the one or more heavy compounds in the stream and at least a portion of the stream as said recycle stream is passed to the transalkylation zone.

2. The method according to claim 1, wherein the separation zone comprises a plurality of distillation zones.

3. The method according to claim 2, wherein the plurality of distillation zones comprises a first distillation zone, a second distillation zone, and a third distillation zone.

4. The method according to claim 3, wherein the first distillation zone produces an overhead stream comprising benzene, and the second distillation zone produces an overhead stream comprising cumene.

5. The method according to claim 4, further comprising converting cumene to phenol.

6. The method according to claim 3, wherein the third distillation zone produces a side-stream comprising di-isopropylbenzene and a bottom stream comprising tri-isopropylbenzene wherein at least a portion of the bottom stream is combined with the side-stream and recycled to the transalkylation zone.

7. The method according to claim 1, wherein the catalyst includes at least one pellet comprising both the first component and the second component.

8. The method according to claim 1, wherein the catalyst includes at least one pellet comprising the first component and at least one other pellet comprising the second component.

9. The method according to claim 8, wherein the catalyst includes a physical mixture of the at least one pellet comprising the first component and the at least one other pellet comprising the second component.

10. The method according to claim 9, wherein the catalyst includes at least one layer comprising at least one pellet comprising the first component and at least one other layer comprising at least one other pellet comprising the second component.

11. A method for processing polyisopropylbenzene for producing cumene, comprising:

A) passing a transalkylation feed stream containing benzene and a recycle stream to a transalkylation zone comprising a catalyst having a first component comprising UZM-8 zeolite and a second component comprising beta zeolite, wherein a weight ratio of the first component to the second component is about 30:70 to about 70:30 under transalkylation conditions to produce a product comprising cumene; and B) passing the reaction product to a separation zone for separating cumene, wherein the separation zone produces a side-stream comprising di-isopropylbenzene and a bottom stream comprising tri-isopropylbenzene and one or more heavy compounds comprising at least one of a hexylbenzene, a heptylbenzene, an indene, a tetralin, a diphenylethane, and a diphenylpropane, wherein at least a portion of the bottom stream is combined with the side-stream and recycled to the transalkylation zone as said recycle stream, and wherein the recycle stream comprises at least about 0.7%, by weight, of the one or more heavy compounds based on the weight of the di-isopropylbenzene, tri-isopropylbenzene, and the one or more heavy compounds in the stream.

12. The method according to claim 11, wherein the catalyst includes at least one pellet comprising both the first component and the second component.

13. The method according to claim 11, wherein the catalyst includes at least one pellet comprising the first component and at least one other pellet comprising the second component.

14. A method for producing cumene, comprising:

A) passing a transalkylation feed stream comprising benzene, di-isopropylbenzene, tri-isopropylbenzene, and at least about 0.7% by weight, one or more heavy compounds based on the weight of the feed stream, wherein the one or more heavy compounds comprises at least one of a hexylbenzene, a heptylbenzene, an indene, a tetralin, a diphenylethane, and a diphenylpropane, to a transalkylation zone to produce a reaction product wherein the transalkylation zone comprises a catalyst comprising a UZM-8 zeolite and a beta zeolite, wherein a weight ratio of the UZM-8 zeolite and the beta zeolite is about 30:70 to about 70:30; and B) passing the reaction product to a separation zone, comprising:
1) a first distillation zone producing an overhead stream comprising benzene;
2) a second distillation zone producing an overhead stream comprising cumene; and
3) a third distillation zone producing a bottom stream comprising:
a) di-isopropylbenzene;
b) tri-isopropylbenzene; and
c) the one or more heavy compounds;
wherein at least a portion of the bottom stream is recycled to the transalkylation zone.

15. The method according to claim 14, wherein the catalyst includes at least one pellet comprising both the UZM-8 zeolite and the beta zeolite.

16. The method according to claim 14, wherein the catalyst includes at least one pellet comprising the UZM-8 zeolite and at least one other pellet comprising the beta zeolite.

* * * * *